United States Patent [19]
Shillington

[11] Patent Number: 5,637,101
[45] Date of Patent: Jun. 10, 1997

[54] QUICK RELEASE NEEDLE COUPLING SYSTEM

[75] Inventor: Richard A. Shillington, Bonsall, Calif.

[73] Assignee: Med-Safe Systems, Inc., Oceanside, Calif.

[21] Appl. No.: 477,929

[22] Filed: Jun. 7, 1995

Related U.S. Application Data

[63] Continuation-in-part of Ser. No. 370,241, Jan. 9, 1995.
[51] Int. Cl.⁶ ........................................... A61M 5/00
[52] U.S. Cl. ...................... 604/242; 604/240; 604/187; 604/110; 604/199
[58] Field of Search ............... 604/51, 110, 181, 604/192, 197–200, 218, 187, 240–243, 263

[56] References Cited

U.S. PATENT DOCUMENTS 3,542,024 11/1970 Burke .................................. 128/221
5,069,225 12/1991 Okamura ............................. 128/765
5,385,555 1/1995 Hausser ............................... 604/192

*Primary Examiner*—Vincent Millin
*Assistant Examiner*—Cris L. Rodriguez
*Attorney, Agent, or Firm*—Baker, Maxham, Jester & Meador

[57] ABSTRACT

A quick release needle holder, comprises a tubular barrel having a needle hub receiving socket and a needle engaging plug on one end, the needle receiving socket having a segmented wall defining a plurality of annular jaws having internal thread segments, the jaws normally biased into an inner position for threadably receiving a needle hub, a cam device slideably mounted on the socket for releaseably biasing the jaws to a needle hub releasing position, and an ejector for engaging the needle hub and ejecting the needle from the plug.

17 Claims, 2 Drawing Sheets

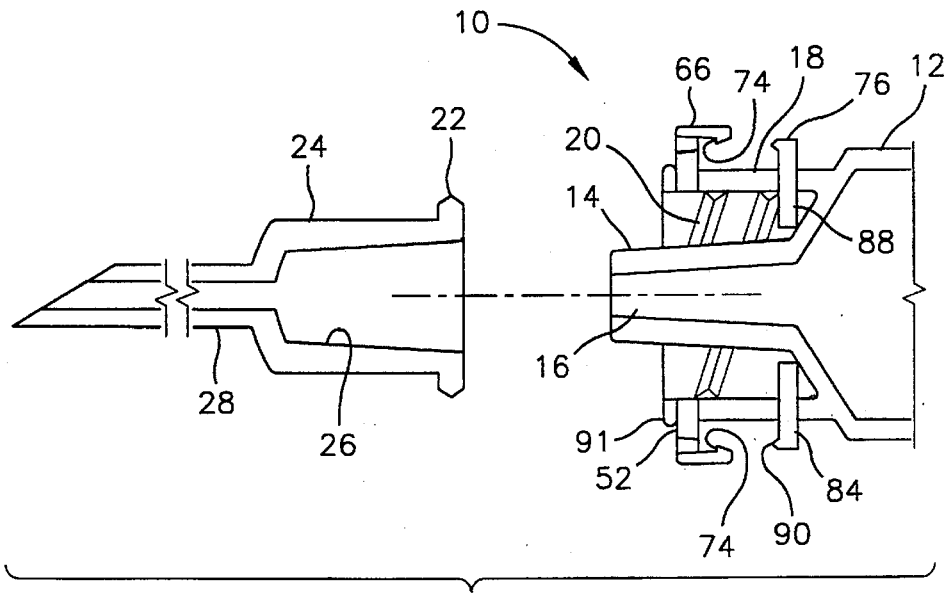
FIG. 1
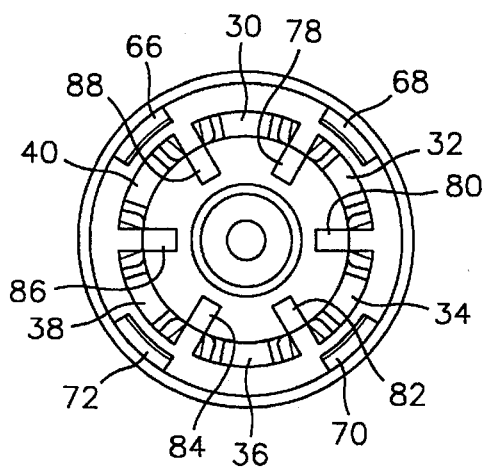
FIG. 2
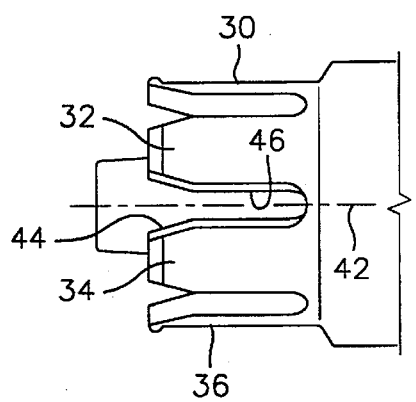
FIG. 3
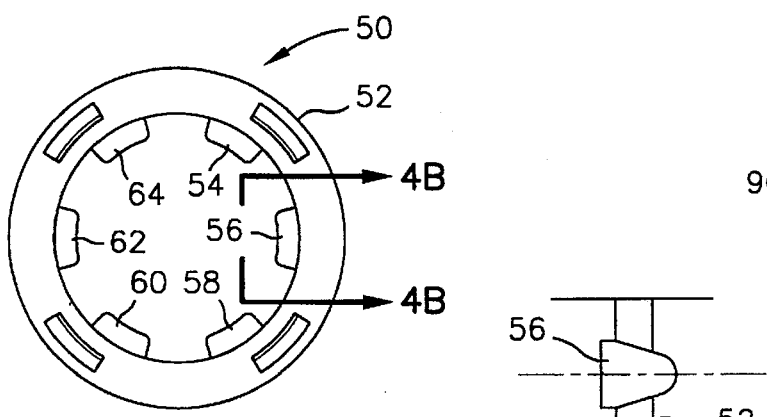
FIG. 4A
FIG. 4B
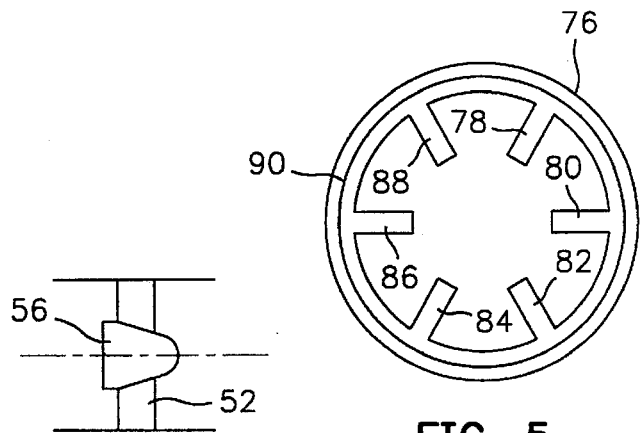
FIG. 5

QUICK RELEASE NEEDLE COUPLING SYSTEM

REFERENCE TO RELATED APPLICATIONS

The present application is a continuation-in-part of co-pending application Ser. No. 08/370,241, filed Jan. 9, 1995, and entitled "QUICK RELEASE NEEDLE REMOVAL APPARATUS".

BACKGROUND OF THE INVENTION

The present invention relates to needle removal devices for syringes and other needle holders and pertains particularly to an improved needle release apparatus for quick and easy removal of needles from syringes.

A huge volume of syringes and hypodermic needles are used daily in the medical and health care industry and must be disposed of safely. These used needles pose a major health problem to the medical personnel using them as well as others who may come into contact with them either innocently or deliberately. The safe and effective disposal of these hypodermic needles poses one of the greatest disposal problems for the medical and health care industry.

Hypodermic needles are widely used for both injection of medication and for withdrawing blood samples for diagnostic purposes. In many instances the needle is removed from the holder and disposed of separately from the holder. In some cases, particularly with certain blood drawing or collection devices, the holder may be reused. In these cases, it is essential that the needle be easily, quickly and safely removed and disposed of without risk to the user.

The typical hypodermic needle comprises an elongated thin cannula having a sharp tip on one end and a hub at or near the other end for detachable attachment to a tubular holder such as a syringe or collector. The hub may have a threaded screw connector, Luer lock, Luer slip, or other type connector. The needle is usually covered with a protective tube or sheath detachably coupled to the hub for hand manipulation to aid in handling and connecting the needle to the holder prior to use. The protective sheath is removed after the needle is mounted in the holder and when it is to be used. The sheath may be again used to protectively cover the needle after use for safer removal and/or removal. However, attempts to reinsert the needle into the sheath often result in pricks of the skin of the user. Therefore, direct disposal of the used needle into a sharps container following use is desirable.

The present common technique of drawing blood samples is by means of an evacuated tube and holder combination such as that sold under the trademark VACUTAINER by the Becton Dickinson Company. These blood collection assemblies comprise a tubular holder or barrel having a double needle in one end, an open end to receive an evacuated collection tube. The needle is threadably mounted in the one end of the tubular holder with an exterior needle for penetrating the patient tissue for receiving blood. The interior needle is covered with a sheath valve and penetrates an elastomeric stopper in one end of an evacuated vacuum tube which acts to draw the blood.

Many devices have been proposed in the past for removal and disposal of the needles. Examples of these are disclosed in the following U.S. Pat. Nos.:

| | |
|---|---|
| Shillington | 4,667,821 |
| Shillington | 4,984,686 |
| Thead et al. | 4,986,811 |
| Sagstetter et al. | 5,086,922 |
| Sagstetter et al. | 5,092,462 |
| Shillington | 5,249,680 |

These prior art devices are generally effective to remove the needles. However, they all have various drawbacks. For example, many of them cannot be effectively used with one hand and require the use of both hands. This is usually difficult or inconvenient for the user may result in the used holder or syringe left laying about.

In the above identified parent application, a needle holder apparatus is disclosed having a novel coupling and means for releasing the needle from the threaded coupling of the holder when it is inserted into a special opening in a container and pressed forward. That apparatus was primarily adapted to holders having a threaded needle coupling.

Most traditional syringes utilize a Luer slip or a Luer lock type of coupling of the needle to the barrel. The Luer slip type of coupling has a tapered hollow plug like fitting extending from the end of the syringe for receiving a tapered socket on the coupling end of the needle. These establish a friction coupling and can be pulled directly off but usually require twisting to release the friction coupling of the needle to the syringe barrel where a tight fit has been established.

The Luer lock type coupling has both a tapered inner plug or sleeve and a threaded outer sleeve coupling. These require relative rotation of from about one quarter to about one half turn to unthread the needle from the outer sleeve coupling of the syringe barrel.

It is desirable that a simple, safe and effective quick release needle coupling for hypodermic needles be available that is applicable to the Luer type needle couplings.

SUMMARY OF THE INVENTION

It is the primary object of the present invention to provide a simple and effective quick release needle coupling for hypodermic needles.

In accordance with a primary aspect of the present invention, a quick release needle holder for hypodermic needles, comprises a tubular barrel having a needle hub receiving socket on one end, said needle receiving socket having a segmented wall defining a plurality of inwardly directed annular threaded segments for receiving and threadably gripping a needle hub, means for normally biasing said segments inwardly to an innermost position for gripping and mounting a needle hub, and means slideably mounted on the socket for biasing the segments open to a hub releasing position, and means for biasing the needle hub off the connector.

BRIEF DESCRIPTION OF THE PREFERRED EMBODIMENTS

The above and other objects and advantages of the present invention will become apparent from the following description when read in conjunction with the accompanying drawings wherein:

FIG. 1 is a side elevation sectional view of a preferred embodiment of the invention;

FIG. 2 is a an end view of the embodiment of FIG. 1;

FIG. 3 is side elevation of the coupling without the camming ring and ejector;

FIG. 4a is a front end view of the camming ring;

FIG. 4b is a view taken on line 4—4 of FIG. 4a;

FIG. 5 is a front end view of the ejector ring;

DETAILED DESCRIPTION OF THE PREFERRED EMBODIMENTS

Figure 6:
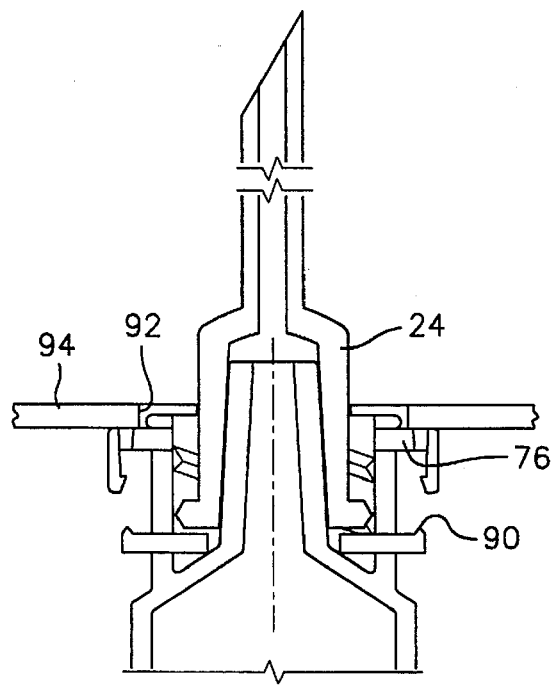
FIG. 6 is a side elevational view showing a needle in a normally installed condition.

Referring to FIG. 1 of the drawings an exemplary embodiment of the invention embodied in a holder such as a syringe barrel is illustrated and designated generally by the numeral 10. A syringe barrel 12, (partially shown) is formed with a modified form of a Luer lock type of coupling for mounting a needle having a socket of the Luer lock type.

As illustrated, barrel 12 is formed with a forwardly extending tubular socket like coupling assembly including a tubular plug 14 having a slightly tapered outer surface. This tubular plug has an internal bore 16 which communicates with the interior of the barrel of the syringe and within the cannula of the needle assembly. An outer sleeve 18 extending concentrically with the tubular plug 14 includes spaced thread-like ridges 20 for cooperative engagement with complimentary thread-like ridges or flanges 22 on a needle hub 24. The needle hub 24 also includes a tapered inner surface 26 for frictionally engaging and sealingly coupling to the plug 14. A needle 28 extends forward from the hub 24 for use in hypodermically injecting drugs, medication and the like.

In the outer sleeve 18 of the modified coupling assembly, the Luer lock type coupling utilizes small cooperative thread-like sections 20. As illustrated they are designed for complete coupling and uncoupling with about ¼ up to ½ half turn or rotation.

The outer sleeve or wall 18 is slotted as shown in FIG. 3 forming multiple segments 30, 32, 34, 36, 38 and 40. These segments form moveable jaws and are formed by a plurality of Y-shaped slots as illustrated, only one of which, 42, will be described. The slot 42 is formed with an outer V-shaped entry portion 44 and an inner straight portion 46, that extends substantially the full length to the base of the socket assembly.

The socket assembly is provided with a camming ring 50, as illustrated in FIG. 4, which comprises a circular body portion 52 having a plurality of small generally wedge-shaped cams 54, 56, 58, 60, 62 and 64, along an inner surface of the ring. These cams preferably have a generally wedge shape, as shown in FIG. 4 to normally rest in the V-shaped entry of the slots. These cams extend into and move along the slots between the segments 30 through 40, for camming them outward to a needle hub releasing position.

The camming ring is also provided with plurality latching fingers 66, 68, 70 and 72, each of which is provided with a latching shoulder 74 for latching the cam ring in the fully cammed position, as will be described.

An ejector ring 76, as illustrated in FIG. 5, mounts around the socket as best seen in FIGS. 1 and 2, and includes ejector fingers 78, 80, 82, 84, 86 and 88, which extend inward through the slots 42 between segments 30 through 40 and operates in conjunction with the camming ring for ejecting the released needle hub from the tubular plug 14. The ejector ring includes an annular ridge 90, that projects outward axially from the face of the ring for engagement by the camming ring to act as a fulcrum as will be more fully discussed. The fingers 78–88 act as levers to pry the needle hub 24 from the tapered plug 14. The ejector may be an inner or outer ring or both with fingers or arms extending through the slots.

In assembling the unit the ejector ring 76 is first placed in position, as shown in FIG. 1 and with the fingers extending into and moved to the bottom of the slots between the segments 30–40. Preferably the fingers form an interference fit with the side walls forming the slots such that the ring is retained in its innermost position as shown. The camming ring is then selected and placed on the end of the socket sleeve 18 and must be forced over an annular shoulder 91, which also functions to retain the camming ring in place on the socket.

Figure 7:
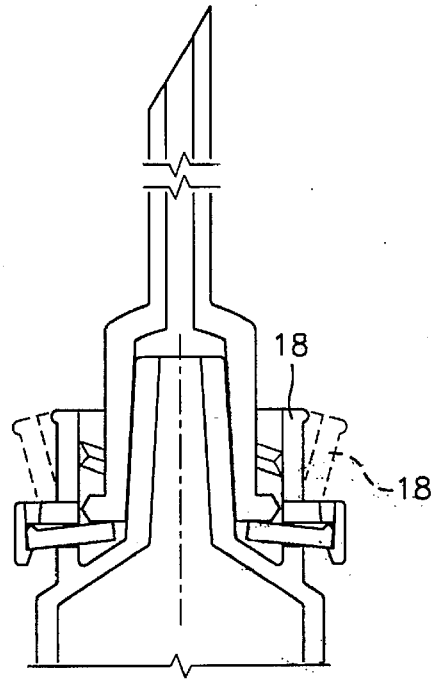
FIG. 7 is a view like FIG. 6 showing the coupling in the ejection position.

In operation, a conventional needle is selected and mounted in the coupling in the traditional fashion of a Luer lock coupling. After the syringe has been used and is ready to be discarded, the needle end of the syringe is inserted into an aperture 92 in a cover 94 of a disposable container, or the like, as shown in FIG. 6, so that the shoulder surrounding and forming the opening or aperture engages the camming ring 50, as shown. As the syringe is pressed forward toward the opening of the container, the camming ring is forced backward along the socket, camming the segments outward as shown in dotted line, releasing the thread segments on the needle hub. The ring is moved further until it engages the annular ridge 90 of the ejector ring as shown in FIG. 7. The force causes the ejector ring 76 to pivot about the base of the slots, causing the fingers 78–80 to engage an inner end of the hub of the needle ejecting it from the surface of the sleeve plug 14, enabling it to drop into the container. The latch fingers on the camming ring extend below the ejector ring, as shown in FIG. 7, so that the latch shoulder 74 engages behind or below the ejector ring latching the camming and ejector rings together at the bottom of the slots. This retains these members in position and the hub of the syringe in the open position to inhibit re-use of the syringe.

Figure 8:
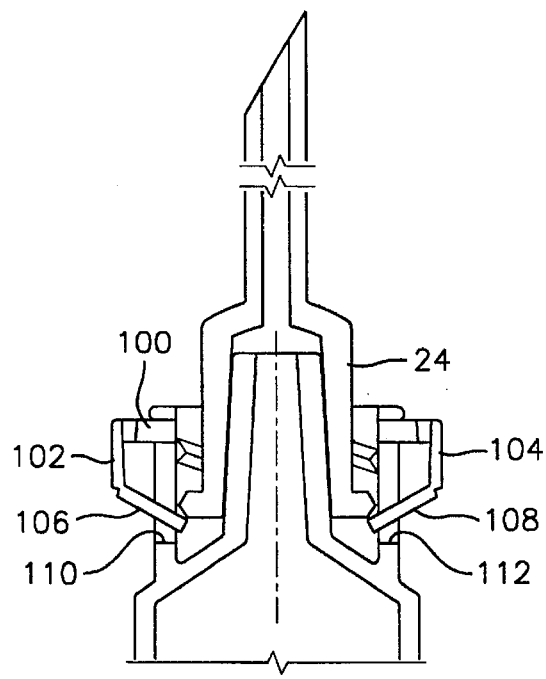
FIG. 8 is view like FIG. 6 showing an alternate embodiment of the invention with a needle in a normally installed condition.
Figure 9:
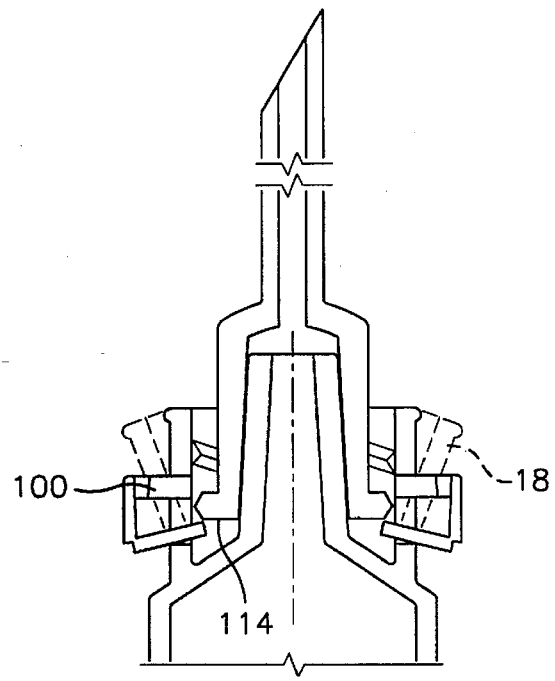
FIG. 9 is a view like FIG. 7 showing the coupling of the FIG. 8 embodiment in the ejection position.

Referring now to FIG. 8 of the drawings, an alternate embodiment is illustrated wherein the camming and ejector rings are combined. The separate ejector ring is eliminated and the camming ring is modified to include a plurality of ejector fingers. In this embodiment all other structures remain the same and are identified by the same reference numerals as in previous embodiments. A combination cam and ejector ring 100 has the same basic configuration as in the previous embodiment with a plurality of axially extending fingers, two, 102 and 104 are in FIGS. 8 and 9. These fingers 102 and 104 include hinged extensions 106 and 108, which extend into the slot below the cam portion of the ring 100 and below the end of the needle hub mounting position, as shown in FIG. 8.

When the syringe has been used and is ready for disposal, the needle end of the syringe is inserted into the opening 92 in a disposable container cover 94, as in the previous embodiment. Pushing the syringe forward cams the segments outward as shown in dashed lines, releasing the hub of the needle. Continued forward motion on the ring moves it downward and engages the fingers 106 and 108 with a bottom edge 110 and 112 of a slot pivoting the fingers 106 and 108 upward like a lever on a fulcrum engaging the end of the lever on an end portion 114 of the needle hub forcing the needle from the surface of the tapered plug 14.

This invention provides a simple and effective means for quick and easy removal of a needle from a syringe without the need for grasping and rotating the needle or the syringe.

While I have illustrated my invention by means of specific embodiments, it is to be understood that numerous changes and modifications may be made therein without departing from the spirit and scope of the invention, as defined in the appended claims.

I claim:

1. A quick release needle coupling for hypodermic needles, comprising:

a tubular barrel having a needle hub receiving socket on one end;

said needle hub receiving socket having an outer wall formed with axially extending slots into a segmented wall defining a plurality of inwardly directed annular jaws;

said jaws normally biased inwardly to an innermost position for receiving and mounting a needle hub;

releasing means slidably mounted on said needle hub receiving socket for biasing said jaws to a needle hub releasing position; and an ejector means mounted on said needle hub receiving socket and responsive to engagement by said releasing means for biasing a needle from said needle hub receiving socket.

2. A needle coupling according to claim 1 wherein said releasing means for releaseably biasing said jaws to a needle hub releasing position comprises a ring and cam means carried by said ring.

3. A needle coupling according to claim 2 wherein said ejector means comprises a ring reciprocally mounted on said needle hub receiving socket and having at least one finger extending inward therefrom.

4. A needle coupling according to claim 1 wherein said means for releaseably biasing said jaws to a needle hub releasing position comprises cam means slidable axially along said slots between said jaws.

5. A needle coupling according to claim 4 wherein said cam means comprises a ring slideably mounted on said needle hub receiving socket.

6. A needle coupling according to claim 1 wherein:

said wall is divided by said slots into six segments; and said means for releaseably biasing said jaws to a needle hub releasing position comprises cam means slidable axially along said slots between said jaws.

7. A needle coupling according to claim 6 wherein said cam means comprises a ring slideably mounted on said needle hub receiving socket.

8. A needle coupling according to claim 7 wherein said segmented wall has an outer end and an inner end and said ring is normally positioned in at said needle hub receiving outer end on said socket.

9. A needle coupling according to claim 8 wherein:

said needle hub receiving socket is defined by a tubular wall which includes an annular shoulder at said outer end thereof; and said ring is normally biased against said shoulder.

10. A needle coupling according to claim 9 wherein:

said means for releaseably biasing said jaws to a needle hub releasing position comprises a ring surrounding said needle hub receiving socket and cam means carried on an inner diameter of said ring; and said ejector means comprises a plurality of fingers carried by said ring and extending inward therefrom through said slots.

11. A quick release needle connector, comprising:

a generally cylindrical tubular barrel having a needle hub connector extending coaxially therefrom on one end;

said needle hub connector comprising a needle hub receiving socket defined by an annular axially extending wall divided by a plurality of axially extending slots into a plurality of segments having internal thread segments and defining a plurality of jaws;

said jaws normally biased into an innermost position for receiving and mounting a needle hub;

releasing means slideably mounted on said needle hub receiving socket for biasing said jaws to a needle hub releasing position; and and ejector means mounted on said needle hub receiving socket and responsive to engagement by said releasing means for biasing a needle from said needle hub receiving socket.

12. A needle connector assembly according to claim 11 wherein releasing means for releaseably biasing said jaws to a needle hub releasing position comprises a ring and a plurality of cams carried by an inner diameter of said ring.

13. A needle connector according to claim 12 wherein said ejector means comprises a ring reciprocally mounted on said needle hub receiving socket and having a plurality of fingers extending inward therefrom through said slots for engagement with a needle hub for ejecting the needle.

14. A needle connector according to claim 13 wherein:

said wall is divided into six segments; and said means for releaseably biasing said jaws to a needle hub releasing position comprises cam means slidable axially along said slots between said jaws.

15. A needle connector according to claim 14 wherein:

said means for releaseably biasing said jaws to a needle hub releasing position comprises a ring surrounding said needle hub receiving socket and cam means carried on an inner diameter of said ring and extending into said slots between said segments; and said ejector means comprises a plurality of fingers carried by said ring and extending inward therefrom through said slots for engagement with said needle hub.

16. A quick releasable needle hub connector assembly, comprising:

an elongated generally cylindrical tubular barrel having a generally tubular needle hub connector extending coaxially on one end;

said needle hub connector comprising necked down tubular axial extension of said tube defining an annular axially extending wall divided by slots into segments defining a plurality of jaws;

said jaws normally biased into an innermost position forming a socket for receiving and mounting a needle hub; and finger operable sleeve including cam means slideably mounted on said barrel for biasing said jaws to a needle releasing position.

17. A needle connector assembly according to claim 16 wherein:

said finger operable sleeve comprises a ring and a plurality of cams on an inner diameter of said ring; and said ejector means comprises a ring reciprocally mounted on said socket and having a plurality of fingers extending inward therefrom through said slots for engagement with a needle hub for ejecting the needle.

* * * * *